United States Patent
Cooperstock et al.

(10) Patent No.: US 12,373,032 B2
(45) Date of Patent: Jul. 29, 2025

(54) METHODS AND SYSTEMS FOR CONTROLLING A HAPTIC DISPLAY

(71) Applicant: THE ROYAL INSTITUTION FOR THE ADVANCEMENT OF LEARNING / MCGILL UNIVERSITY, Montréal (CA)

(72) Inventors: Jeremy Cooperstock, Westmount (CA); Antoine Weill-Duflos, Verdun (CA); Juliette Regimbal, Verdun (CA); Nusaiba Radi, Montreal (CA); Jeffrey Blum, Montreal (CA); Parisa Alirezaee, Montreal (CA); Yukai Zhang, Montreal (CA)

(73) Assignee: THE ROYAL INSTITUTION FOR THE ADVANCEMENT OF LEARNING / MCGILL UNIVERSITY, Montreal (CA)

( * ) Notice: Subject to any disclaimer, the term of this patent is extended or adjusted under 35 U.S.C. 154(b) by 147 days.

(21) Appl. No.: 17/917,761

(22) PCT Filed: Apr. 7, 2021

(86) PCT No.: PCT/CA2021/050461
§ 371 (c)(1),
(2) Date: Oct. 7, 2022

(87) PCT Pub. No.: WO2021/203197
PCT Pub. Date: Oct. 14, 2021

(65) Prior Publication Data
US 2023/0168738 A1 Jun. 1, 2023

Related U.S. Application Data

(60) Provisional application No. 63/006,141, filed on Apr. 7, 2020.

(51) Int. Cl.
G08B 23/00 (2006.01)
A61B 5/00 (2006.01)
G06F 3/01 (2006.01)

(52) U.S. Cl.
CPC .............. G06F 3/016 (2013.01); A61B 5/742 (2013.01); A61B 5/7455 (2013.01)

(58) Field of Classification Search
CPC ....... G06F 3/016; A61B 5/742; A61B 5/7455; A61B 5/486; A61B 5/021; A61B 5/024; A61B 5/145
See application file for complete search history.

(56) References Cited

U.S. PATENT DOCUMENTS 8,004,391 B2 * 8/2011 Cruz Hernandez .... A61B 5/165
340/407.1
8,390,218 B2 3/2013 Houston et al.
(Continued)

OTHER PUBLICATIONS

Maclean et al., "Perceptual Design of Haptic Icons", 2003, University of British Columbia.
(Continued)

Primary Examiner — Toan N Pham
(74) Attorney, Agent, or Firm — NORTON ROSE FULBRIGHT CANADA LLP (57) ABSTRACT

Methods and systems for controlling a haptic display are provided. Data associated with first and second data types is obtained, the data defining values for the first and second data types. The first and second data types are associated to first and second vibration features of the haptic display, respectively, the second vibration feature different from the first vibration feature. A vibration pattern comprising a plurality of vibration pulses representing the first and second vibration features within a common time interval is produced on the haptic display, wherein the first vibration feature is expressed based on the values of the data for the (Continued)

first data type and the second vibration feature is expressed based on the values of the data for the second data type.

22 Claims, 7 Drawing Sheets

(56) References Cited

U.S. PATENT DOCUMENTS

| | | | |
|---|---|---|---|
| 9,049,998 B2 | 6/2015 | Brumback et al. | |
| 10,228,764 B2* | 3/2019 | Levesque | A61B 5/0002 |
| 10,276,001 B2* | 4/2019 | Smith, IV | G06F 3/016 |
| 10,504,339 B2* | 12/2019 | Birnbaum | G08B 6/00 |
| 11,376,087 B2* | 7/2022 | Verner | A61B 90/03 |
| 2006/0003812 A1 | 1/2006 | Moody et al. | |
| 2019/0325716 A1* | 10/2019 | Khoshkava | G08B 6/00 |

OTHER PUBLICATIONS

Brewster et al., "Tactons: Structured Tactile Messages for Non-Visual Information Display", vol. 28. Australian Computer Society, 2004, 15-23.
Ryu et al., "Vibrotactile Feedback for Information Delivery in the Vehicle", IEEE Transactions on Haptics 3(2):138-149, 2010, DOI: 10.1109/TOH.2010.1.
Alirezaee et al., Exploring the Effectiveness of Haptic Alarm Displays for Critical Care Environments, IEEE Haptics Symposium (Haptics), 2020, pp. 948-954, DOI: 10.1109/HAPTICS45997.2020. ras.HAP20.156.6c3cc0bf.
Barralon et al., "Development and Evaluation of Multidimensional Tactons for a Wearable Tactile Display", MobileHCI '07: 9th international conference, 2007, DOI: 10.1145/1377999.137800.
Lim et al., "TouchPhoto: Enabling Independent Picture Taking and Understanding for Visually-Impaired Users", Lecture Notes in Electrical Engineering, 2019, DOI: 10.1007/978-981-13-3194-7_62.
Fontana De Vargas et al., "Speaking Haptically: From Phonemes to Phrases With a Mobile Haptic Communication System", IEEE Trans Haptics, 202; 14(3):479-490. doi: 10.1109/TOH.2021. 3054812.
Ternes et al., "Designing Large Sets of Haptic Icons with Rhythm", Lecture Notes in Computer Science, 2008, DOI: 10.1007/978-3-540-69057-3_24.
Yoo et al., "Consonance of Vibrotactile Chords", IEEE Transactions on Haptics 7(1):3-13, 2014, DOI: 10.1109/TOH.2013.57.
Park et al., "Perceptual Space of Amplitude-Modulated Vibrotactile Stimuli", IEEE World Haptics Conference, 2011, DOI: 10.1109/WHC.2011.5945462.
Culbertson et al., "WAVES: A Wearable Asymmetric Vibration Excitation System for Presenting Three-Dimensional Translation and Rotation Cues", CHI Conference on Human Factors in Computing Systems pp. 4972-4982, 2017, DOI: 10.1145/3025453. 3025741.
Blum et al., "Single-Actuator Vibrotactile Numeric Information Delivery in the Face of Distraction", IEEE World Haptics Conference, 2019, DOI: 10.1109/WHC.2019.8816082.
Vyas et al., "HapToes: Vibrotactile Numeric Information Delivery via Tactile Toe Display", IEEE Haptics Symposium, 2020, DOI: 10.1109/HAPTICS45997.2020.ras. HAP20.34.8ad689d4.
Regimbal et al., "Single-Actuator Simultaneous Haptic Rendering for Multiple Vital Signs", Lecture Notes in Computer Science, 2020.
Houtsma, Adrianus J. M., "Estimation of mutual information from limited experimental data", Journal of the Acoustical Society of America 74 (1983): 1626-1629.
Durlach et al., "Resolution in one dimension with random variations in background dimensions", Attention Perception & Psychophysics, 46(3):293-296, 1989, DOI: 10.3758/BF03208094.
Azadi et al., "Evaluating Vibrotactile Dimensions for the Design of Tactons", IEEE Transactions on Haptics, 7(1):14-23, 2014, DOI: 10.1109/TOH.2013.2296051.
Chen et al., "Design and Evaluation of Identifiable Key-Click Signals for Mobile Devices", IEEE Transactions on Haptics, 4(4):229-241, 2011, DOI: 10.1109/TOH.2011.21.
Sherrick, Carl E., "A scale for rate of tactual vibration." The Journal of the Acoustical Society of America vol. 78, Pt 1 (1985): 78-83, 1985, DOI: 10.1121/1.392457.
Sofia, Katherine O., "Mechanical and Pyschophysical Studies of Surface Wave Propagation during Vibrotactile Stimulation" IEEE Transactions on Haptics, vol. 6, Issue 3, 2012, DOI: 10.1109/TOH. 2013.1.
Cholewiak et al., "Vibrotactile Targeting in Multimodal Systems: Accuracy and Interaction", IEEE 14th Symposium on Haptics, 2006, DOI: 10.1109/HAPTIC.2006.1627100.
Brown et al., "Multidimensional Tactons for Non-Visual Information Presentation in Mobile Devices", IEEE 14th Symposium on Haptics, 2006, DOI: 10.1109/HAPTIC.2006.1627100.
Lee et al., "BuzzWear: Alert Perception in Wearable Tactile Displays on the Wrist", CHI '10: Proceedings of the SIGCHI Conference on Human Factors in Computing Systems, p. 433-442, 2010, DOI: 10.1145/1753326.17533.
Tan et al., "Information transmission with a multifinger tactual display", Perception & Psychophysics, 61(6):993-1008, 1999.
Park et al., "Haptic Enchanters: Attachable and Detachable Vibrotactile Modules and Their Advantages", IEEE Transactions on Haptics, vol. 12, Issue 1, 2018, DOI: 10.1109/TOH.2018.2859955.
Tan et al., "Methodology for Maximizing Information Transmission of Haptic Devices: A Survey", Proceedings of the IEEE, vol. 108 Issue: 6, 2020, DOI: 10.1109/JPROC.2020.2992561.
Chan et al., "Learning and Identifying Haptic Icons under Workload", First Joint Eurohaptics Conference, 2005, DOI: 10.1109/WHC.2005.86.
Rabinowitz et al., "Multidimensional tactile displays: Identification of vibratory intensity, frequency, and contactor area", The Journal of the Acoustical Society of America 82, 1243, 1987, DOI: 10.1121/1.395260.
Blum et al., "Expressing Human State via Parameterized Haptic Feedback for Mobile Remote Implicit Communication", Proceedings of the 7th Augmented Human International Conference, 2016.
Blum et al., "Pseudo-Ambience: Filling the Gap Between Notifications and Continuous Information Displays", Proceedings of the 7th Augmented Human International Conference, 2016.
Stoelting, Robert K., "APSF Stresses Use of Audible Monitor Alarms", The Official Journal of the Anesthesia Patient Safety Foundation, vol. 19, No. 2, 17-28, 2004.
Berglund et al., "Guidelines for Community Noise", World Health Organization, 1999.
Brown et al., "A First Investigation into the Effectiveness of Tactons", IEEE First Joint Eurohaptics Conference, 2005, DOI: 10.1109/WHC.2005.6.
Cvach, Maria, "Monitor alarm fatigue: an integrative review" Biomed Instrum Technol, 46(4):268-77, 2012, DOI: 10.2345/0899-8205-46.4.268.
Darbyshire et al., "An investigation of sound levels on intensive care units with reference to the WHO guidelines", Crit Care, 3;17(5):R187, 2013, DOI: 10.1186/cc12870.
Ferris et al., "Continuously Informing Vibrotactile Displays in Support of Attention Management and Multitasking in Anesthesiology", Hum Factors, 53(6):600-11, 2011, DOI: 10.1177/0018720811425043.
Formby et al., "The role of frequency selectivity in measures of auditory and vibrotactile temporal resolution", J Acoust Soc Am, 91(1):293-305, 1992, DOI: 10.1121/1.402772.
Franzen, Ove, "Vibrotactile Frequency Discrimination", Perception & Psychophysics, 17(5), 480-484, 1975, DOI: 10.3758/BF03203298.
Gomes et al., "The evaluation of tactile parameters and display prototype to support physiological monitoring and multitasking for anesthesia providers in the operating room", IEEE Trans Haptics, 13(3):628-644, 2020, DOI: 10.1109/TOH.2019.2960017.

(56) References Cited

OTHER PUBLICATIONS

Katzman et al., "Evaluation of tactile cues for simulated patients' status under high and low workload", Proceedings of the Human Factors and Ergonomics Society Annual Meeting, 63(1):658-662, 2019, DOI: 10.1177/1071181319631285.

Blum et al., "Habituation to Pseudo-Ambient Vibrotactile Patterns for Remote Awareness", IEEE Haptics Symposium, 2020, DOI: 10.1109/HAPTICS45997.2020.ras.HAP20.153.550dbcba.

Ng et al., "Vibro-Monitor: A Vibrotactile display for Physiological Data Monitoring", 2004.

Otenio et al., "Noise level in a 222 bed hospital in the 18th health region—PR", Braz J Otorhinolaryngol, 73 (2):245-50, 2007, DOI: 10.1016/s1808-8694(15)31073-9.

Sendelbach et al., "Alarm Fatigue: A Patient Safety Concern", AACN Adv Crit Care, 24(4):378-86, 2013, DOI: 10.1097/NCI.0b013e3182a903f9.

Van Erp et al., "Tactile Torso Display as Countermeasure to Reduce Night Vision Goggles Induced Drift" Spatial Disorientation in Military Vehicles: Causes, Consequences and Cures, 49-1-49-8, 2003.

Xie et al., "Clinical review: The impact of noise on patients' sleep and the effectiveness of noise reduction strategies in intensive care units", Crit Care, 13(2):208, 2009, DOI: 10.1186/cc7154.

Yao et al., "Design and analysis of a recoil-type vibrotactile transducer", The Journal of the Acoustical Society of America, vol. 128, 128(2):619-27, 2010, DOI: 10.1121/1.3458852.

Brewster et al., "Non-visual information display using tactons", CHI '04 Extended Abstracts on Human Factors in Computing Systems, 787-788, 2004, DOI: 10.1145/985921.985936.

Brown et al., "Tactile crescendos and sforzandos: applying musical techniques to tactile icon design", CHI '06 Extended Abstracts on Human Factors in Computing Systems, 610-615, 2006, DOI: 10.1145/1125451.1125578.

Lee et al., "Real-time perception-level translation from audio signals to vibrotactile effects", CHI '13: Proceedings of the SIGCHI Conference on Human Factors in Computing Systems, 2567-2576, 2013, DOI: 10.1145/2470654.2481354.

Brewster et al., "An Investigation into the Use of Tactons to Present Progress Information", Human-Computer Interaction—Interact 2005, 6-17, DOI: 10.1007/11555261_4.

Sullivan et al., "Multi-Sensory Stimuli Improve Distinguishability of Cutaneous Haptic Cues", IEEE Transactions on Haptics, vol. 13, Issue 2, 2019, DOI: 10.1109/TOH.2019.2922901.

Raza et al., "Pneumatically Controlled Wearable Tactile Actuator for Multi-Modal Haptic Feedback", IEEE Access, vol. 12, 2024, DOI: 10.1109/ACCESS.2024.3376753.

Hwang et al., "Real-Time Dual-Band Haptic Music Player for Mobile Devices", IEEE Transactions on Haptics, vol. 6, Issue 3, 2013, DOI: 10.1109/TOH.2013.7.

Talhan et al., "Tactile Ring: Multi-Mode Finger-Worn Soft Actuator for Rich Haptic Feedback", IEEE Access PP(99):1-1, DOI: 10.1109/ACCESS.2019.2961430.

* cited by examiner

METHODS AND SYSTEMS FOR CONTROLLING A HAPTIC DISPLAY

CROSS-REFERENCE TO RELATED APPLICATIONS

The present application is a US National Stage of International Application No. PCT/CA2021/050461, filed on Apr. 7, 2021, which claims priority from U.S. Provisional Application No. 63/006,141, entitled "MULTI-SIGNAL RENDERING THROUGH A SINGLE HAPTIC ACTUATOR" and filed on Apr. 7, 2020, the entire contents of which are incorporated herein by reference.

TECHNICAL FIELD

The improvements generally relate to the field of human-computer interfaces, and more specifically to the use of haptic actuators.

BACKGROUND

Humans interact with computers and other electronic devices in a variety of ways, both to provide information to an electronic device, and to receive information therefrom. Some approaches for receiving information from electronic devices include screens and other visual displays, speakers and other audible displays, as well as vibration devices or the like Haptic displays of various types are used in smartphones and other electronic devices to provide information to a user via vibration or other forces which can produce stimuli for a sense of touch of a user. Existing approaches for use of haptic displays to provide information to a user rely on the user holding a device in their hand, or having haptic displays affixed to their skin. Other existing approaches rely on multiple haptic displays, which may need to be positioned at various specific locations on a user.

Therefore, improvements may be desirable

SUMMARY

In accordance with a broad aspect, there is provided a method for controlling a haptic display. Data associated with first and second data types is obtained, the data defining values for the first and second data types. The first and second data types are associated to first and second vibration features of the haptic display, respectively, the second vibration feature different from the first vibration feature. A vibration pattern comprising a plurality of vibration pulses representing the first and second vibration features within a common time interval is produced on the haptic display, wherein the first vibration feature is expressed based on the values of the data for the first data type and the second vibration feature is expressed based on the values of the data for the second data type.

In at least some embodiments in accordance with any one or more of the previous embodiments, the producing of the vibration pattern comprises producing a count of vibration pulses within the common time interval at a vibration tempo, wherein the first vibration feature is the vibration tempo, and wherein the second vibration feature is the count of vibration pulses.

In at least some embodiments in accordance with any one or more of the previous embodiments, the obtaining of the data associated with the first and second data types comprises obtaining a heart rate of a subject and a blood pressure of the subject.

In at least some embodiments in accordance with any one or more of the previous embodiments, the method comprises: obtaining additional data associated with at least one third data type, the additional data defining additional values for the at least one third data type; and associating the at least one third data type to at least one third vibration feature of the haptic display, the at least one third vibration feature different from the first and second vibration features; wherein the producing, on the haptic display, of the vibration pattern comprises producing the plurality of vibration pulses to represent the at least one third vibration feature within the common time interval, wherein the at least one third vibration feature is expressed based on the additional values for the at least one third data type.

In at least some embodiments in accordance with any one or more of the previous embodiments, the producing of the vibration pattern comprises producing a count of vibration pulses within the common time interval at a vibration tempo, wherein the first vibration feature is the vibration tempo, wherein the second vibration feature is the count of vibration pulses, and wherein one of the at least one third vibration features is a frequency composition of the vibration pulses.

In at least some embodiments in accordance with any one or more of the previous embodiments, the obtaining of the data associated with the first and second data types comprises obtaining a heart rate of a subject and a blood pressure of the subject, and wherein the obtaining of the additional data associated with the at least one third data type comprises obtaining a level of peripheral oxygen saturation of the subject.

In at least some embodiments in accordance with any one or more of the previous embodiments, the producing of the plurality of vibration pulses to represent the at least one third vibration feature within the common time interval comprises producing the vibration pulses with one of dissonant frequency compositions and consonant frequency compositions to express the additional values for the at least one third data type.

In at least some embodiments in accordance with any one or more of the previous embodiments, the producing of the vibration pattern comprises producing a count of vibration pulses within the common time interval at a vibration tempo, wherein the first vibration feature is the vibration tempo, wherein the second vibration feature is the count of vibration pulses, and wherein one of the at least one third vibration features is an intensity of the vibration pulses.

In at least some embodiments in accordance with any one or more of the previous embodiments, the common time interval defines four beats.

In at least some embodiments in accordance with any one or more of the previous embodiments, the first vibration feature being expressed based on the values of the data for the first data type comprises selecting one of a plurality of first discrete states of the first vibration feature based on the values of the data of the first data type, and wherein the second vibration feature being expressed based on the values of the data for the second data type comprises selecting one of a plurality of second discrete states of the second vibration feature.

In at least some embodiments in accordance with any one or more of the previous embodiments, the first and second pluralities of discrete states are associated with low, normal, and high values for the data of the first and second data types relative to predetermined ranges for the first and second data types.

In accordance with another broad aspect, there is provided a system for controlling a haptic display. The system comprises a processing unit and a non-transitory computer-readable medium. The computer readable medium has stored thereon computer-readable instructions which are executable by the processing unit for: obtaining data associated with first and second data types, the data defining values for the first and second data types; associating the first and second data types to first and second vibration features of the haptic display, respectively, the second vibration feature different from the first vibration feature; and producing, on the haptic display, a vibration pattern comprising a plurality of vibration pulses representing the first and second vibration features within a common time interval, wherein the first vibration feature is expressed based on the values of the data for the first data type and the second vibration feature is expressed based on the values of the data for the second data type.

In at least some embodiments in accordance with any one or more of the previous embodiments, the producing of the vibration pattern comprises producing a count of vibration pulses within the common time interval at a vibration tempo, wherein the first vibration feature is the vibration tempo, and wherein the second vibration feature is the count of vibration pulses.

In at least some embodiments in accordance with any one or more of the previous embodiments, the obtaining of the data associated with the first and second data types comprises obtaining a heart rate of a subject and a blood pressure of the subject.

In at least some embodiments in accordance with any one or more of the previous embodiments, the computer-readable instructions are executable for: obtaining additional data associated with at least one third data type, the additional data defining additional values for the at least one third data type; and associating the at least one third data type to at least one third vibration feature of the haptic display, the at least one third vibration feature different from the first and second vibration features; wherein the producing, on the haptic display, of the vibration pattern comprises producing the plurality of vibration pulses to represent the at least one third vibration feature within the common time interval, wherein the at least one third vibration feature is expressed based on the additional values for the at least one third data type.

In at least some embodiments in accordance with any one or more of the previous embodiments, the producing of the vibration pattern comprises producing a count of vibration pulses within the common time interval at a vibration tempo, wherein the first vibration feature is the vibration tempo, wherein the second vibration feature is the count of vibration pulses, and wherein one of the at least one third vibration features is a frequency composition of the vibration pulses.

In at least some embodiments in accordance with any one or more of the previous embodiments, the obtaining of the data associated with the first and second data types comprises obtaining a heart rate of a subject and a blood pressure of the subject, and wherein the obtaining of the additional data associated with the at least one third data type comprises obtaining a level of peripheral oxygen saturation of the subject.

In at least some embodiments in accordance with any one or more of the previous embodiments, the producing of the plurality of vibration pulses to represent the at least one third vibration feature within the common time interval comprises producing the vibration pulses with one of dissonant frequency compositions and consonant frequency compositions to express the additional values for the at least one third data type.

In at least some embodiments in accordance with any one or more of the previous embodiments, the producing of the vibration pattern comprises producing a count of vibration pulses within the common time interval at a vibration tempo, wherein the first vibration feature is the vibration tempo, wherein the second vibration feature is the count of vibration pulses, and wherein one of the at least one third vibration features is an intensity of the vibration pulses.

In at least some embodiments in accordance with any one or more of the previous embodiments, the common time interval defines four beats.

In at least some embodiments in accordance with any one or more of the previous embodiments, the first vibration feature being expressed based on the values of the data for the first data type comprises selecting one of a plurality of first discrete states of the first vibration feature based on the values of the data of the first data type, and wherein the second vibration feature being expressed based on the values of the data for the second data type comprises selecting one of a plurality of second discrete states of the second vibration feature.

In at least some embodiments in accordance with any one or more of the previous embodiments, the first and second pluralities of discrete states are associated with low, normal, and high values for the data of the first and second data types relative to predetermined ranges for the first and second data types.

Features of the systems, devices, and methods described herein may be used in various combinations, in accordance with the embodiments described herein. In particular, any of the above features may be used alone, together in any suitable combination, and/or in a variety of arrangements, as appropriate.

BRIEF DESCRIPTION OF THE DRAWINGS

In the drawings.

It will be noted that throughout the appended drawings, like features are identified by like reference numerals.

DETAILED DESCRIPTION

The use of haptic displays to convey information to a user can provide a variety of benefits over visual or audible displays, particularly in environments which are either very audibly noisy, or in which low noise levels are desirable. For example, nurses, doctors, and other health practitioners in hospitals may be required to process a wide variety of information, some of which is provided using audible alarms or other audible signals. However, it may be desirable for hospitals to generally provide low-noise environments for their patients, their staff, and other persons present at the hospital. The present disclosure provides techniques and/or approaches for the use of haptic displays to provide multiple types of information concurrently, for instance for use by health practitioners. It should be understood, however, that the systems, methods, devices, computer-readable media, and other aspects of the present disclosure are considered for use in a variety of contexts and operating environments.

Figure 1A:
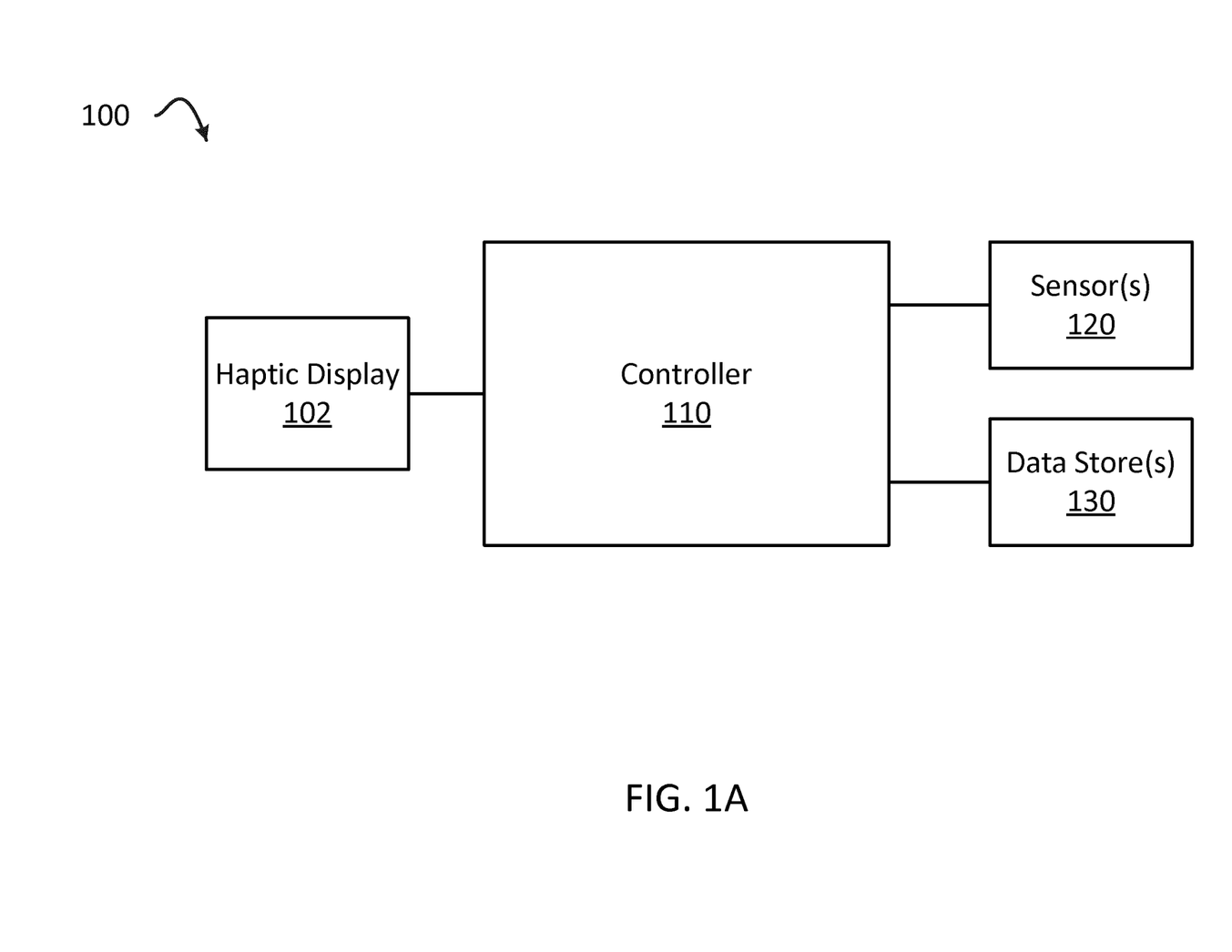
FIG. 1A is a block diagram of an example system for controlling a haptic display.

With reference to FIG. 1A, there is illustrated a system 100 for controlling a haptic display, for instance the haptic display 102. The haptic display 102 is coupled to a controller 110, which can issue commands and other signals to the haptic display 102 to effect control thereof. The controller 110 can be any suitable kind of electrical or electronic device, and can include one or more microcontrollers, one or more field-programmable gate arrays (FPGAs), one or more computing devices, one or more mobile devices, or the like. The controller 110 can be coupled to the haptic display 102 in any suitable fashion, including one or more wired communication paths, one or more wireless communication paths, or any suitable combination thereof. The communication protocols used to mediate communication between the haptic display 102 and the controller 110 can include any suitable types of communication protocols.

The haptic display 102 can be any suitable type of haptic device via which information can be transmitted to a user. In some embodiments, the haptic display 102 includes a vibration device, for instance a voice-coil actuator (VCA), a piezoelectric actuator, an electro-active polymer, an eccentric rotating mass (ERM) actuator, a linear resonant actuator (LRA), or any other suitable type of vibration device. In some other embodiments, the haptic display 102 can include other types of vibration devices.

The controller 110 controls the haptic display 102 to deliver data to a user by producing vibration pulses, which act as stimuli for a sense of touch of the user. In contrast with uses of haptic displays to simulate a particular sensation or provide a particular experience, as may be the case in the context of a vibrating gamepad or a motion-enabled seat, the haptic display 102 is controlled by the controller 110 to convey particular data to the user, which the user is to recognize based on the particular stimuli perceived by the sense of touch of the user. The haptic display 102 can be controlled to convey data in a variety of fashions via the vibration pulses. As will be described in greater detail hereinbelow, the haptic display 102 is configured for producing vibration pulses in accordance with a plurality of vibration features to convey the aforementioned data. The vibration features can be used to convey multiple pieces of information of different data types to the user concomitantly, or within a common time interval, while using a singular haptic display 102. As used herein, a "data type" refers to data relating to one particular parameter or characteristic amongst a plurality of parameters or characteristics in a given setting.

Figure 1B:
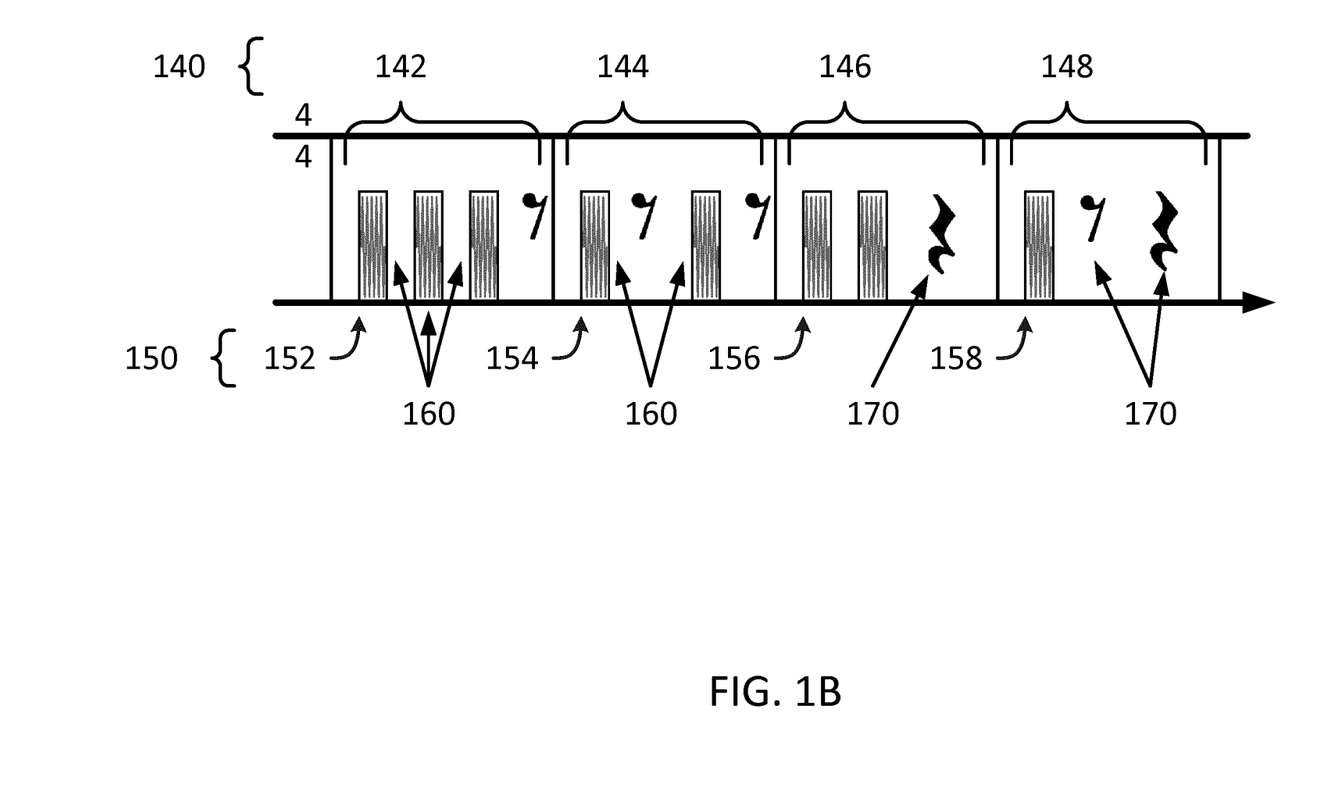
FIG. 1B is a graphical representation of example four-beat vibration patterns produced on the haptic display of FIG. 1A.

With additional reference to FIG. 1B, the haptic display 102 can be controlled to produce a vibration pattern, which may be presented once, or which may be repeated over a plurality of time intervals. To illustrate the vibration patterns, a commonly-used musical notation of "measures" or "bars", each containing a predetermined number of "beats", is employed. Data is conveyed by the haptic display 102 via one or more vibration patterns 140, (FIG. 1B illustrates four vibration patterns 142, 144, 146, and 148), which are presented in the one or more time intervals 152, 154, 156, 158 (collectively "time intervals 150"), or measures using the musical notation analogy. In the example illustrated in FIG. 1B, each vibration pattern 140 is composed of up to four vibration pulses 160, and thus each one of the time intervals 150 is composed of four beats in the musical notation analogy. It should be noted that in other examples, the vibration patterns 140 may include up to any suitable number of vibration pulses 160, and would be represented by time intervals 150 having a commensurate number of beats in the musical notation analogy. It should additionally be noted that a vibration pulse 160 is not necessarily produced for each beat (as denoted by rest markers 170, employing the musical notation of crotchets and quavers); put differently, some beats in any given time interval 150 may not include a vibration pulse 160 (i.e., be silent). In addition, each vibration pulse 160 can be a vibration at a single frequency, or can have a frequency composition which includes multiple frequency components, mirroring the concept of chords from the musical notation analogy. Vibration pulses having a frequency composition are composed of temporally-overlapping vibration components of different frequencies. For example, a vibration pulse can include vibration components at 60 Hz and at 80 Hz, which are produced concurrently. The present disclosure uses the term "vibration features" to refer to different modifiable parameters of the vibration patterns 140 produced by the haptic display 102. The vibration features of the haptic display 102 are used to convey different information and can include, for example, a tempo of vibration, a number of vibration pulses per time interval 150 (i.e., how many beats are vibration pulses vs. silent), the frequency composition of a vibration pulse (i.e., the frequencies of the vibration components which compose a vibration pulse), the intensity (or amplitude) of the vibration pulses, or the like. The vibration features, used to produce the vibration pulses 160, are used to express data, and different ones of the vibration features can be used to communicate data of different types, as will be described in greater detail hereinbelow.

For example, the haptic display 102 can be controlled to produce vibration pulses 160 in a series of four-beat time intervals 150. The number of vibration pulses 160 performed in each time interval 150 is a first vibration feature used to express the values of a first data type to a user of the haptic display 102. The tempo of the time intervals 150, i.e. the rate at which time intervals 150 and beats within time intervals 150 are produced by the haptic display 102, is a second vibration feature and is used to express the values of a second data type to the user. To convey additional data types, the frequency composition of the vibration pulses used for each vibration pattern can be varied, the intensity of the vibration pulses can be varied, or the like, or any suitable combination thereof. For instance, different frequency compositions (e.g. dissonant compositions, consonant compositions, etc.) can be used to express different values for a third data type. In another instance, different frequency compositions are used to express different values for a third data type, and the intensity of the vibration pulses are used to express the values for a fourth data type. Other approaches, including using other vibration features to provide additional information, are considered.

Referring back to FIG. 1A, the controller 110 can be coupled to one or more sensors 120 and/or one or more data stores 130 which provide information to the controller 110 for conveyance to the user via the haptic display 102. In some embodiments, the sensors 120 include one or more sensors deployed in an environment in which the user is operating or otherwise present. For example, the sensors 120 include a blood pressure sensor, a heartbeat sensor, and/or a peripheral oxygen saturation sensor, which can be used to collect data from a subject in a hospital or other clinical setting. In other examples, the sensors 120 can be other types of sensors used in industrial settings, commercial settings, or any other type of setting. The sensors 120 can include any suitable number of sensors, as appropriate, such as but not limited to a heart rate sensor, a blood pressure sensor, an oxygenation level sensor, flow rate sensor, a pressure sensor, a temperature sensor, a positional sensor, and the like.

The data stores 130 can be any suitable repository of information which can be conveyed to the user via the haptic display 102. The controller 110 can be coupled to the data stores 130 via any suitable communication paths, including wired and/or wireless communication paths. In some embodiments, the data stores 130 are located remotely from the controller 110, and the controller 110 can access the information stored therein via one or more networks, for instance the Internet, or one or more private networks, for instance a local or wide-area intranet. In some embodiments, the data stores 130 can include dynamically-generated information, for instance simulation data, for instance to simulate real-life situations for training purposes. In some embodiments, the dynamically-generated information can be generated in real-time.

In some embodiments, the controller 110 and the haptic display 102 are integrated as a single device. The controller 110 and the haptic display 102 can be encased in a casing or other enclosure which can also contain a power source, for instance a battery, a communication unit, for instance for communicating with the data stores 130 and/or with remotely-accessible sensors 120, and/or any other suitable elements. Remote communication with the data stores 130 and/or with the sensors 120 can be performed, for instance, substantially in real-time. In some other embodiments, the enclosure which contains the controller 110 and the haptic display 102 can also contain one or more sensors 120, which can be coupled to the haptic display 102 via the controller 110 for displaying of information gathered by the sensors 120 substantially in real-time. Other approaches are also considered.

Figure 2:
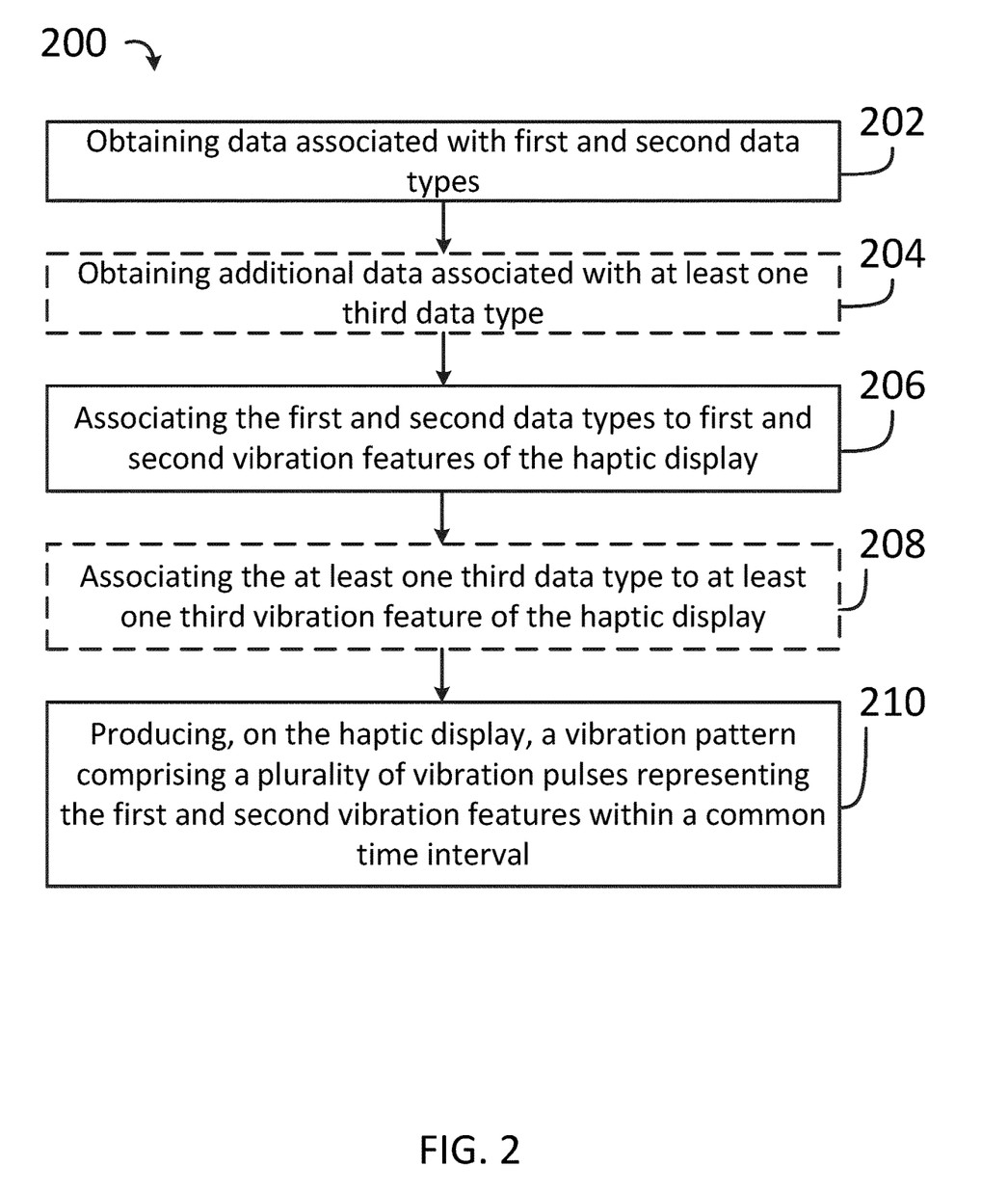
FIG. 2 is a flowchart illustrating an example method for controlling a haptic display.

With reference to FIG. 2, there is illustrated a method 200 for controlling a haptic device, for instance the haptic display 102. At step 202, data associated with first and second data types is obtained. In some embodiments, the data is received as a plurality of data streams, each associated with a respective one of the first and second data types. For example, the method 200 can be used in a clinical setting, and different types of data relating to a given clinical subject (e.g., a patient) are received. This can include data about a subject heart rate, a subject blood pressure, a subject peripheral oxygen saturation ($SpO_2$) level, a subject red blood cell count, a subject glucose level, or any other suitable subject data. In another example, the method 200 can be used in a data analysis setting, in which data are received from a data store, for instance the data store 130, and the data obtained as part of step 202 relate to different types of entries or different columns of data stored in the data store 130. Obtaining the data can include storing a local copy of the data obtained from the sensors 120 and/or from the data stores 130, or obtaining a real-time stream of data, for instance from the sensors 120.

In some embodiments, at step 204, additional data associated with at least one third data type is obtained. The additional data can be received in substantially similar fashion to the data associated with the first and second data types received at step 202, or in any other suitable fashion.

At step 206, the first data type is associated with a first vibration feature of the haptic display 102, and a second data type is associated with a second vibration feature of the haptic display 102. The association can be performed in the controller 110, or can be indicated by the data type, for instance in metadata or similar data stored in conjunction with the data type. For example, a data type of heart rate can be associated with a first one of the vibration features, for instance the vibration tempo, and a data type of blood pressure can be associated with a second one of the vibration features, for instance the number of vibration pulses per time interval. Other associations are also considered.

In some embodiments, at step 208, a third one of the plurality of data types is associated to a third vibration feature of the haptic display 102. The association can be performed in the controller 110, or can be indicated by the data type, for instance in metadata or similar data stored in conjunction with the data type. For example, a data type of subject $SpO_2$ level can be associated with a third one of the vibration features, such as the frequency composition of the vibration pulses, the intensity of the vibration pulses, or the like. Other associations are also considered. In this fashion, in some embodiments the haptic display 102 is used to present information regarding two data types to the user, and, in some other embodiments, the haptic display 102 is used to present information regarding three or more data types to the user. In addition, the method 200 can include any number of additional steps in which supplemental data types are associated with respective vibration features of the haptic display 102.

At step 210, a vibration pattern is produced on the haptic display. The vibration patterns are composed of a plurality of vibration pulses representing the first and second vibration features within a common time interval. The first vibration feature is expressed based on the values of the data obtained at step 202 which is associated with the first data type, and the second vibration feature is expressed based on the values of the data obtained at step 202 which is associated with the second data type. For example, changes in the subject heart rate result in changes in the tempo of vibration pulses produced using the first vibration feature, and changes in the subject blood pressure result in changes in the number of vibration pulses per time interval. It should be understood that the vibration pattern may also represent the one or more third vibration features, which are expressed based on the values of the data obtained at step 204 which is associated with the at least one third data type. For example, changes in the subject $SpO_2$ levels result in changes in the frequency composition of the vibration pulses. Other approaches are also considered.

In some embodiments, the vibration features—tempo of vibration pulses, number of vibration pulses per time interval, a frequency composition of vibration pulses, and the like—are expressed by selecting one of a plurality of discrete states for each vibration feature, based on the values for the data of the associated data type. For example, the tempo of the vibration pattern is associated with a subject heart rate, and the tempo is set at one of three discrete states depending on the values for the subject heart rate. Similarly, the number of vibration pulses per time interval is associated with a subject blood pressure, and the number of vibration pluses is set at one of three discrete states depending on the subject heart rate. Table 1 hereinbelow lists one example implementation (bpm refers to beats-per-minute; Hz refers to Hertz):

TABLE 1

| Data Type | Vibration Feature | Low Values | Normal Values | High Values |
|---|---|---|---|---|
| Heart Rate | Tempo | 80 bpm | 160 bpm | 320 bpm |
| Blood Pressure | Vibration pulses per Time Interval | 1 vibration pulse | 2 vibration pulses | 3 vibration pulses |
| $SpO_2$ | Frequency composition | 80 Hz & 25.2 Hz | 80 Hz (single frequency) | 80 Hz & 190.2 Hz |

In this example, normal values for a subject heart rate are set between 41 and 159 bpm: when a subject's heart rate is below 41 bpm, the haptic display 102 will produce the vibration pattern to express the first vibration feature with a tempo of 80 bpm; when a subject's heart rate is between 41 and 159 bpm, the haptic display 102 will produce the vibration pattern to express the first vibration feature with a tempo of 160 bpm; and when a subject's heart rate is above 159 bpm, the haptic display 102 will produce the vibration pattern to express the first vibration feature with a tempo of 320 bpm. It should be noted that the particular tempo (i.e., the tempo value in bpm) at which the vibration patterns are expressed is not intended to represent a direct, one-to-one mapping of the subject heart rate. Rather, the tempo at which the vibration patterns are expressed is selected, for instance from a set of discrete tempo values, based on the subject heart rate.

It should also be understood that the values for the tempo of the vibration pattern can be tuned to different values, for example based on user preference or other factors. Similarly, normal values for a subject blood pressure and $SpO_2$ levels can be set as desired, and the second and third vibration features can be expressed based on the values for blood pressure and $SpO_2$ values, for instance as obtained from the sensors 120. Implementations in other contexts are also considered.

Figure 3:
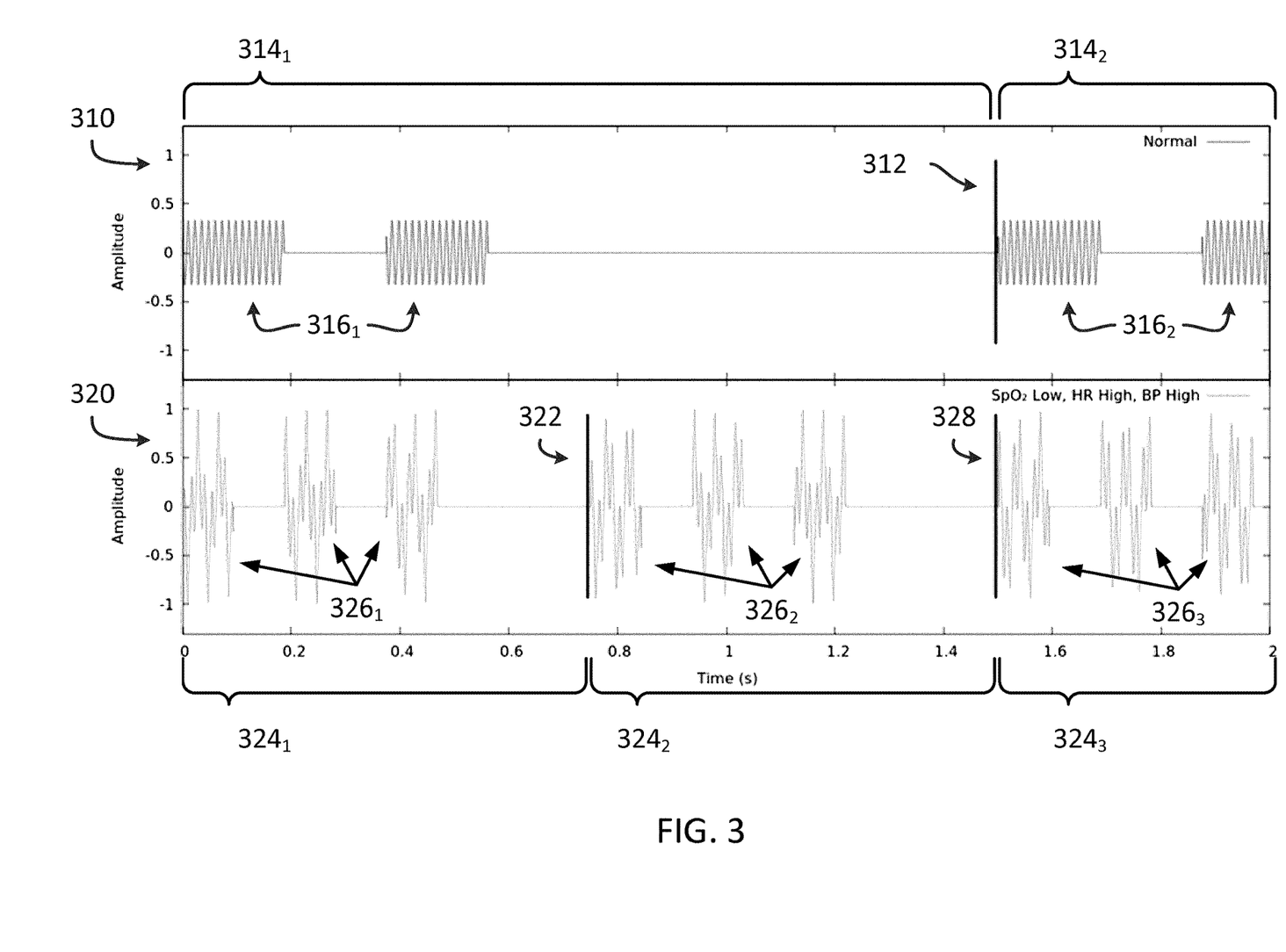
FIG. 3 illustrates different example vibration outputs of a haptic display.

With additional reference to FIG. 3, two examples of vibration patterns 310 and 320 are illustrated, produced by the haptic display 102 using the example values of Table 1. The vibration pattern 310 is for a subject having normal values for heart rate, blood pressure, and $SpO_2$. A first time interval $314_1$ contains two vibration pulses $316_1$ at 80 Hz (i.e., single frequency), and the vibration pattern 310 is presented at a tempo of 160 bpm. A second time interval $314_2$, beginning after the marker 312, also contains two vibration pulses $316_2$ at 80 Hz, and is presented at the tempo of 160 bpm.

The vibration pattern 320 is for a subject having a high heart rate, high blood pressure, and a low $SpO_2$ level. A first time interval $324_1$, located prior to the marker 322, contains three vibration pulses $326_1$, which have a frequency composition of 80 Hz and 25.2 Hz. A second time interval $324_2$ is located between the markers 322 and 328, and similarly contains three vibration pulses $326_2$, as does a third time interval $324_3$, which is located after the marker 328 and contains three vibration pulses $326_3$.

As illustrated in FIG. 3, depending on the values for the three data types considered (in this example: heart rate, blood pressure, $SpO_2$ levels), the vibration pulses produced by the haptic display 102 vary. These changes in vibration pattern can be used to convey information about the subject's condition to a user with only the single haptic display 102. In addition to requiring a singular device, the use of the haptic display 102 instead of sound-based alarms or other alerting systems can result in a reduction in noise produced in the environment in which the user and subject are present.

In some embodiments, the method 200 is performed periodically, such that vibration patterns like those illustrated in FIG. 3 are presented via the haptic display 102 in a periodic fashion. For example, in a clinical setting, the system 100 is configured for controlling the haptic display 102 to periodically present vibration patterns based on clinical data obtained about a health state of a subject of a healthcare intervention. As changes in the clinical data occur, the vibration patterns are also updated to reflect the changes. As a result, the user of the haptic display 102 can understand changes in the clinical data by detecting changes in the vibration patterns presented via the haptic display 102.

In this fashion, the user of the haptic display 102 does not need to distinguish between different vibration patterns in the abstract, or in a proverbial vacuum; rather, the user of the haptic display 102 can understand the clinical data by detecting changes in the vibration patterns over time. Put differently, the user of the haptic display 102 does not need to, for example, recognize the tempo of vibration pulses as being 160 bpm, or that three vibration pulses are being played in each time interval. Instead, the user of the haptic display 102 can identify transitions in the vibration patterns, for instance from 80 bpm to 160 bpm, or between dissonant and consonant frequency compositions, and recognize changes in the clinical data based on these transitions. In some embodiments, the periodic presentation of vibration patterns to the user via the haptic display 102 can result in improved recognition of the data presented via the haptic display 102.

Figure 4:
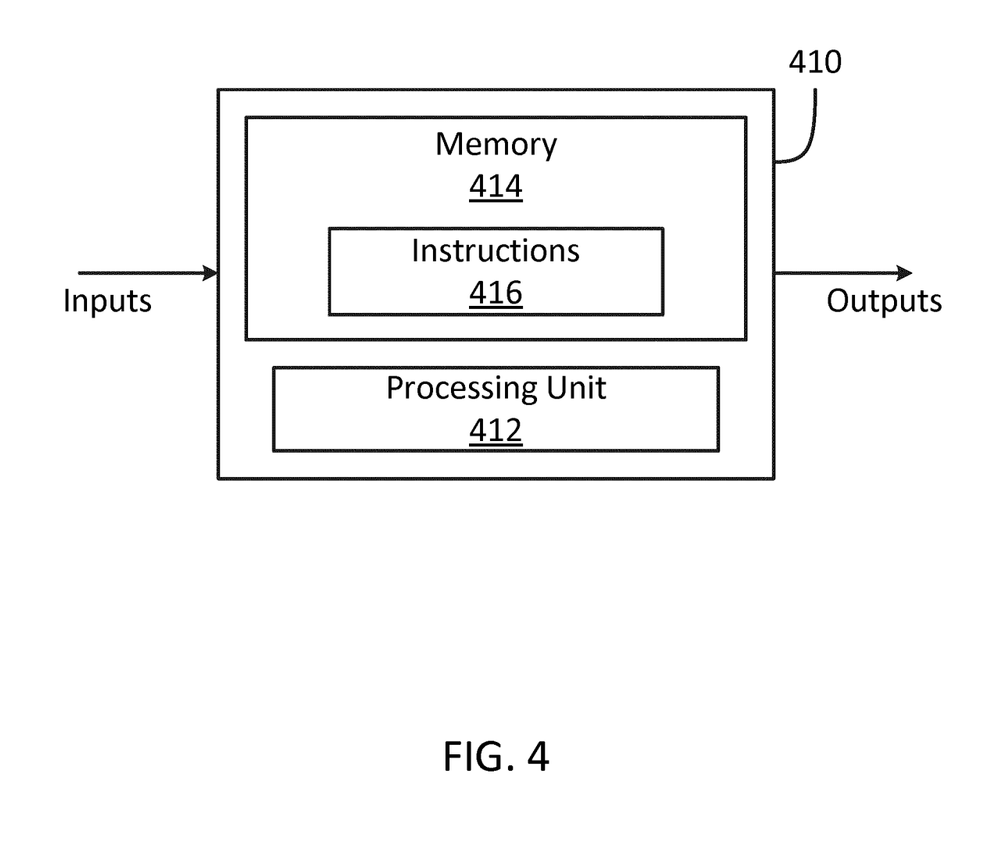
FIG. 4 is a block diagram of an example computing system for controlling a haptic display.

With reference to FIG. 4, the method 200 may be implemented by a computing device 410, comprising a processing unit 412 and a memory 414 which has stored therein computer-executable instructions 416. For example, the controller 110 can be embodied as the computing device 410.

The processing unit 412 may comprise any suitable devices configured to implement the method 200 such that instructions 416, when executed by the computing device 410 or other programmable apparatus, may cause the functionality of the controller 110 described herein to be implemented. The processing unit 412 may comprise, for example, any type of general-purpose microprocessor or microcontroller, a digital signal processing (DSP) processor, a central processing unit (CPU), an integrated circuit, a field-programmable gate array (FPGA), a reconfigurable processor, other suitably programmed or programmable logic circuits, or any combination thereof.

The memory 414 may comprise any suitable known or other machine-readable storage medium. The memory 414 may comprise non-transitory computer readable storage medium, for example, but not limited to, an electronic, magnetic, optical, electromagnetic, infrared, or semiconductor system, apparatus, or device, or any suitable combination of the foregoing. The memory 414 may include a suitable combination of any type of computer memory that is located either internally or externally to device, for example random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), ferroelectric RAM (FRAM) or the like. Memory 414 may comprise any storage means (e.g., devices) suitable for retrievably storing machine-readable instructions 416 executable by processing unit 412.

In one example implementation, the haptic display 102 may be embodied as a vibrotactile actuator which may be affixed to a wrist of a user, for instance via a band, strap, bracelet, or the like. The vibrotactile actuator is configured to produce vibration patterns representing four vibration features: a tempo of vibration pulses, a number of vibration pulses per time interval, a frequency composition of vibration pulses, and an intensity of vibration pulses. The four vibration features are associated with respective data types for data relating to a particular operational context, for instance a medical operations scenario, an industrial processing scenario, or the like. In some embodiments, the presentation of vibration patterns may be performed in a substantially periodic fashion, such that information relating to the operational context is presented to the user periodically. In some other embodiments, the presentation of vibration patterns may be performed punctually, for instance in response to changes in the values of the data for the data types, or the like.

Figure 5:
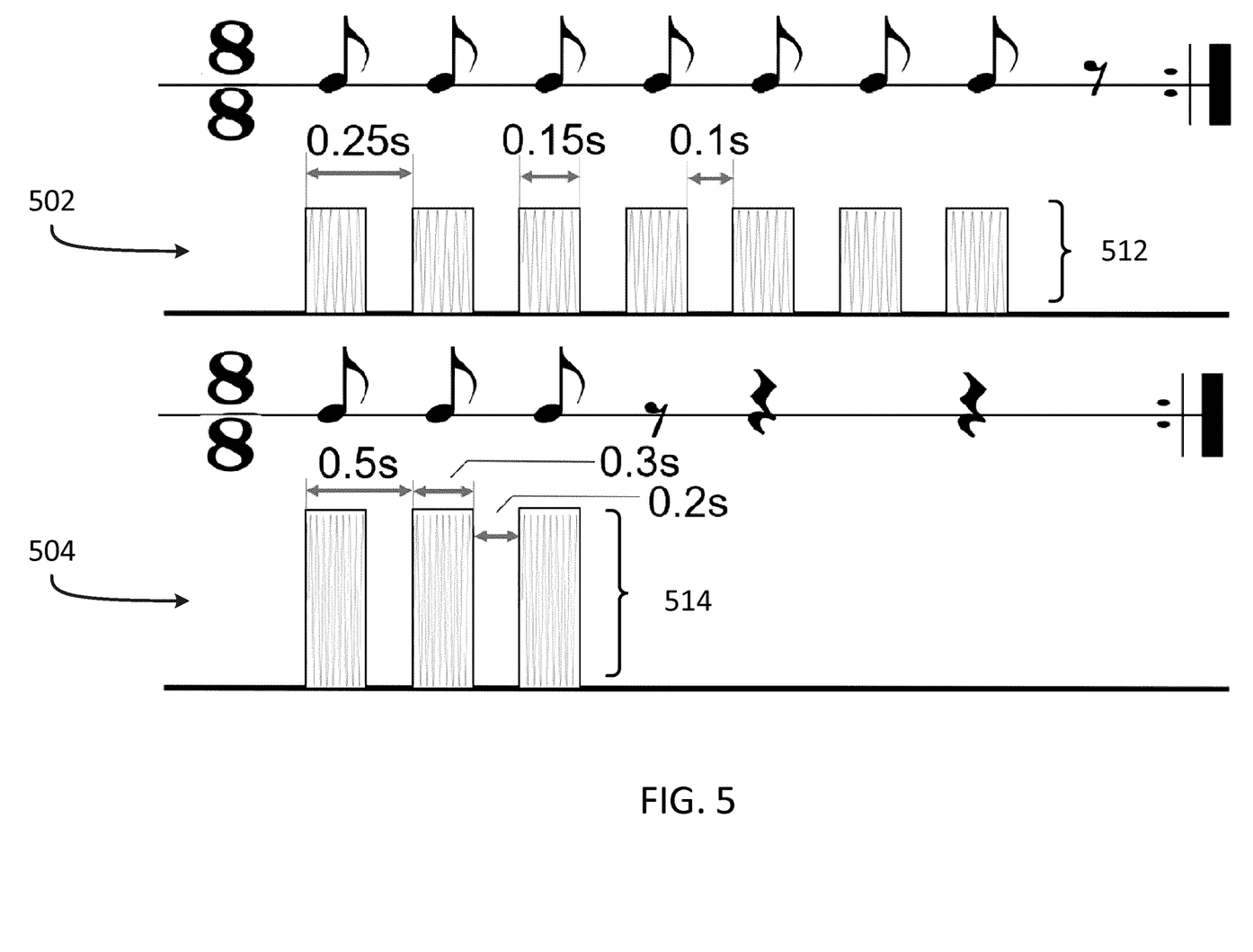
FIG. 5 is a graphical representation of example eight-beat vibration patterns produced on the haptic display of FIG. 1A.

With reference to FIG. 5, in this example implementation, the vibration patterns produced by the vibrotactile actuator employ a time interval analogous to an eight-beat measure. Each vibration pattern 502, 504 presents a number of sequential vibration pulses selected from the group of {1, 2, 3, 5, 7} vibration pulses (though other counts of vibration pulses could be presented in other example implementations). The remainder of each time interval are rests (i.e., silent); for instance, a time interval including 3 sequential vibration pulses would be followed by 5 rests. The tempo of the vibration patterns is assigned one of three values, slow, moderate and fast, which can correspond to specific bpm values (e.g., 120 bpm, 240 bpm, 480 bpm). In some cases, the frequency composition of the vibration pulses is selected such that no frequency component is used multiple times. For instance, three frequency compositions are considered: 60 Hz+80 Hz, 160 Hz (single frequency), and 320 Hz+360 Hz. Two vibration intensities are considered, namely weak and strong. In practice, the specific amplitude of vibration used to produce the weak and strong vibration intensities may be configurable by a user to account for differences in perceived intensity.

Thus, in this example, each eighth of the time intervals has a duration of 0.5 seconds (s), 0.25 s, or 0.125 s, depending on the tempo. With a duty-cycle of 60%, the duration (i.e., pulse widths) of the vibration pulses are 0.3 s, 0.15 s, and 0.075 s for slow, moderate, and fast tempos, respectively. The combination of the four vibration features permits multidimensional stimuli with 90 states. In FIG. 5, the vibration pattern 502 demonstrates a pattern with 7 weak intensity vibration pulses 512 at 240 BPM, and vibration pattern 504 demonstrates a pattern with 3 strong intensity vibration pulses 514 at 120 BPM.

In one example experimental setting, an application was developed to generate the vibration patterns and record responses from experiment participants. The application may be operated on any suitable implementation of computing device 410, for instance a tablet computer. Vibrotactile signals are transmitted through an audio output channel of the tablet (e.g., an audio jack). In some cases, the vibrotactile signals are amplified using any suitable type of signal processing device (e.g., an audio amplifier), and presented to the experiment participants on the haptic display 102, which may be embodied as a voice-coil actuator. The haptic display may be worn on the glabrous part of the non-dominant wrist of the experiment participants, and secured with a Velcro strap or similar device. To mask audible cues from the vibration pulses produced by the haptic display 102, experiment participants are provided with noise-reduction earplugs and over-ear headphones to play pink noise Experiment sessions may begin with a preliminary stage to perform intensity equalization and to familiarize the user with the vibrations produced by the haptic display 102, for instance with guidance of the person running the experiment. As part of the intensity equalization, each experiment participant was asked to identify adequate, distinguishable levels of intensity corresponding to "weak" and "strong" vibration pulses that were perceived as having equivalent intensity across different frequencies. The familiarization involves at least 10 minutes of vibration patterns being presented to the user and attempts by the user to identify the vibration patterns (i.e., to identify the tempo, vibration pulse count, frequency composition, and/or intensity of the vibration pulses in different vibration patterns). Once familiarized with the vibration patterns, the experiment participants carried out the remainder of the experiment on their own.

In some embodiments, the experiments consist of a training block and a plurality of testing blocks (e.g., six training blocks). The training block consists of a number of trials, which may include a number of randomly-selected vibration patterns, and a number of vibration patterns identified as difficult to identify (e.g., based on a pilot study). For example, the training block can include 20 randomly-selected vibration patterns, and 20 "difficult" vibration patterns. The experiment participant is asked to identify the vibration pattern, and is provided with the correct identification thereafter. The testing blocks also consist of a number of trials involving presenting the experiment participant with different vibration patterns for identification, without providing the correct identification thereafter. The vibration patterns presented to the experiment participant may be repeated periodically over a predetermined interval, or may be presented only a predetermined number of times, or over a fixed time period. For example, the vibration patterns of the trials may only be presented for 4 seconds: in this example, a vibration pattern having a high tempo (e.g. 480 bpm) could be presented four times, whereas a vibration pattern having a low tempo (e.g. 120 bpm) could be presented only once. In some cases, the presentation of the vibration patterns to the experiment participant is performed in response to the experiment participant interacting with a "Play" button or similar element of an interface of the tablet computer.

Figure 6A:
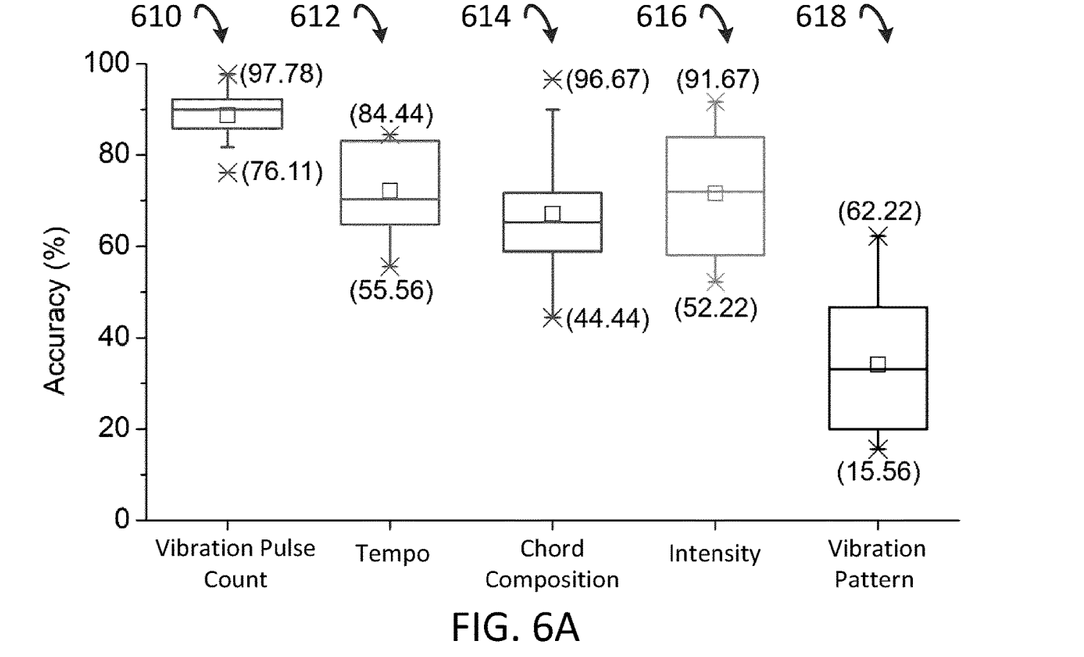
FIGS. 6A-6B are example boxplot graphs of accuracy results of an experimental setup using the haptic display of FIG. 1A.
Figure 6B:
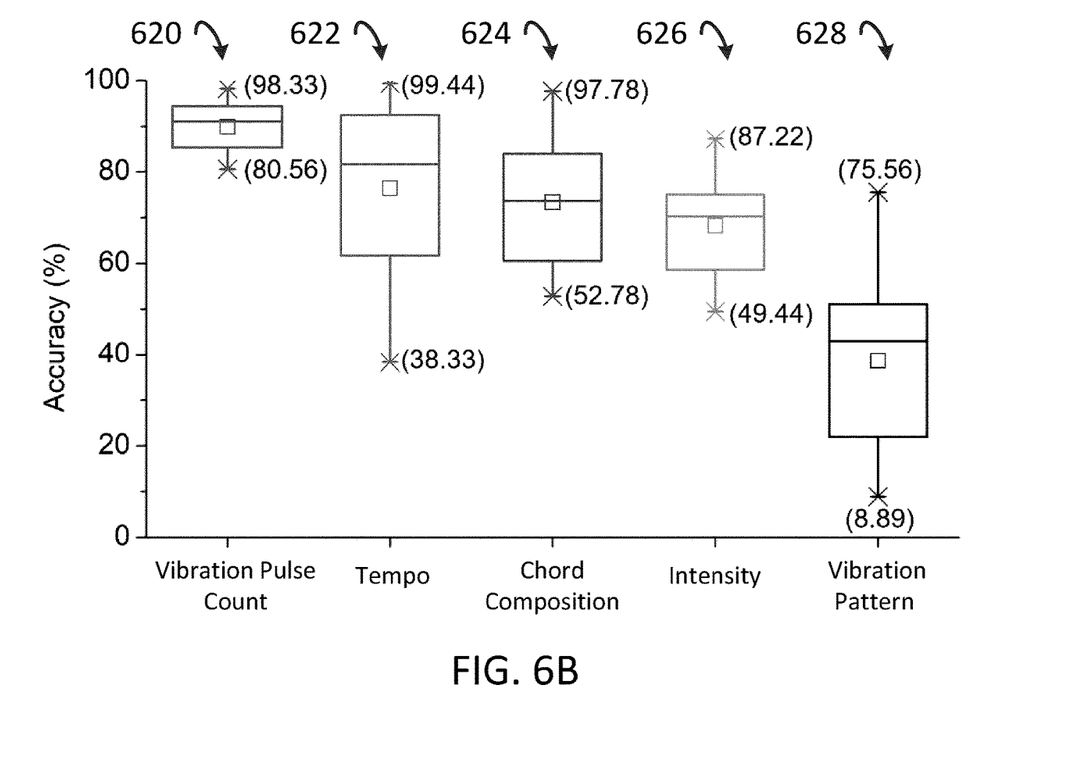

With reference to FIGS. 6A-6B, example boxplot graphs of accuracy results for two instances of the experimental setup described hereinabove are presented: FIG. 6A for an instance of the experimental setup in which the vibration patterns were presented repeatedly, and FIG. 6B for an instance of the experimental setup in which the vibration patterns were presented only once. The boxplot graphs of FIGS. 6A-B include accuracy results for each of the vibration features independently, as well as for the vibration patterns as a whole. In FIG. 6A, the accuracy of the four vibration features are indicated via boxplots 610 (vibration pulse count), 612 (tempo), 614 (frequency composition) and 616 (intensity). Boxplot 618 indicates the accuracy of reporting for the vibration patterns as a whole, that is to say, the accuracy with which experiment participants correctly identified all four vibration features. In FIG. 6B, the accuracy of the four vibration features are indicated via boxplots 620 (vibration pulse count), 622 (tempo), 624 (frequency composition) and 626 (intensity). Boxplot 628 indicates the accuracy of reporting for the vibration patterns as a whole, that is to say, the accuracy with which experiment participants correctly identified all four vibration features. Of note, the differences in accuracy between the experimental setup of FIG. 6A and those of FIG. 6B are not statistically significant.

In some embodiments, the accuracy results of FIGS. 6A-6B may be used to estimate an amount of information provided by the vibration patterns, known as an "information transfer" (IT) value. The IT value may be determined using established methods known in the art, including Houtsma's method and/or Durlach's general additivity law. The IT value may also be determined on the basis of confusion matrices, which evaluate the number of trials in which a particular vibration feature was mistaken for another particular vibration feature. On the basis of Houtsma's method and confusion matrices, the IT value for the example instances of FIGS. 6A-6B may be estimated to approximately 3.06 bits. The range of the estimated IT value of the participants is 1.937 to 5.425 bits, with a geometric mean of 3.933 bits. This range is indicative of considerable individual differences in perception and/or identification of vibration patterns.

Following the experiment sessions, additional information may be collected from the experiment participants, for instance by way of a post-experiment survey. In the example, experiment participants indicated that frequency composition and intensity were the most difficult vibration parameters to identify, and indicated that vibration pulse count and tempo were the easiest vibration parameters to identify. Certain experiment participants also indicated that the low-intensity 160 Hz vibration pattern felt similar to the high-intensity 320 Hz+360 Hz vibration pattern. Certain other experiment participants indicated that the tempo vibration parameter was difficult to identify when the vibration count pulse is low.

The results of the experiment sessions indicate that when the vibration patterns were presented periodically, correct identification of the intensity vibration feature was easier, and correct identification of frequency composition was harder. The converse was true when the vibration patterns were presented only a predetermined number of times (e.g., once). Of the individual vibration features, the vibration pulse count was the most likely to be correctly identified. Changes to the duration of the vibration pulses may also have an impact on correct identification of the vibration features.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

The term "connected" or "coupled to" may include both direct coupling (in which two elements that are coupled to each other contact each other) and indirect coupling (in which at least one additional element is located between the two elements).

The embodiments disclosed herein may be provided in the form of a software product which may be adapted to operate one or more types of haptic devices, and is configured in accordance with the specifications and capabilities of the haptic device(s) employed in a given implementation. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

The embodiments described in this document provide non-limiting examples of possible implementations of the present technology. Upon review of the present disclosure, a person of ordinary skill in the art will recognize that changes may be made to the embodiments described herein without departing from the scope of the present technology. Yet further modifications could be implemented by a person of ordinary skill in the art in view of the present disclosure, which modifications would be within the scope of the present technology.

What is claimed is:

1. A method for controlling a haptic display, comprising:
obtaining data associated with first and second data types, the data defining values for the first and second data types, the first data type relating to a first parameter of a plurality of measurable parameters associated with an operating environment of the haptic display, and the second data type relating to a second parameter of the plurality of parameters, the second parameter different from the first parameter;
associating the first and second data types to first and second vibration features of the haptic display, respectively, the second vibration feature different from the first vibration feature; and
producing, on the haptic display, a vibration pattern comprising a plurality of vibration pulses representing the first and second vibration features within a common time interval, the first vibration feature relating to a first parameter of the vibration pattern and the second vibration feature relating to a second parameter of the vibration pattern, wherein the first vibration feature is expressed based on the values of the data for the first data type and the second vibration feature is expressed based on the values of the data for the second data type.

2. The method of claim 1, wherein the producing of the vibration pattern comprises producing a count of vibration pulses within the common time interval at a vibration tempo, wherein the first vibration feature is the vibration tempo, and wherein the second vibration feature is the count of vibration pulses.

3. The method of claim 2, wherein the obtaining of the data associated with the first and second data types comprises obtaining a heart rate of a subject and a blood pressure of the subject.

4. The method of claim 1, comprising:
obtaining additional data associated with at least one third data type, the additional data defining additional values for the at least one third data type; and associating the at least one third data type to at least one third vibration feature of the haptic display, the at least one third vibration feature different from the first and second vibration features;

wherein the producing, on the haptic display, of the vibration pattern comprises producing the plurality of vibration pulses to represent the at least one third vibration feature within the common time interval, wherein the at least one third vibration feature is expressed based on the additional values for the at least one third data type.

5. The method of claim 4, wherein the producing of the vibration pattern comprises producing a count of vibration pulses within the common time interval at a vibration tempo, wherein the first vibration feature is the vibration tempo, wherein the second vibration feature is the count of vibration pulses, and wherein one of the at least one third vibration features is a frequency composition of the vibration pulses.

6. The method of claim 5, wherein the obtaining of the data associated with the first and second data types comprises obtaining a heart rate of a subject and a blood pressure of the subject, and wherein the obtaining of the additional data associated with the at least one third data type comprises obtaining a level of peripheral oxygen saturation of the subject.

7. The method of claim 5, wherein the producing of the plurality of vibration pulses to represent the at least one third vibration feature within the common time interval comprises producing the vibration pulses with one of dissonant frequency compositions and consonant frequency compositions to express the additional values for the at least one third data type.

8. The method of claim 4, wherein the producing of the vibration pattern comprises producing a count of vibration pulses within the common time interval at a vibration tempo, wherein the first vibration feature is the vibration tempo, wherein the second vibration feature is the count of vibration pulses, and wherein one of the at least one third vibration features is an intensity of the vibration pulses.

9. The method of claim 1, wherein the first vibration feature being expressed based on the values of the data for the first data type comprises selecting one of a plurality of first discrete states of the first vibration feature based on the values of the data of the first data type, and wherein the second vibration feature being expressed based on the values of the data for the second data type comprises selecting one of a plurality of second discrete states of the second vibration feature.

10. The method of claim 9, wherein the first and second pluralities of discrete states are associated with low, normal, and high values for the data of the first and second data types relative to predetermined ranges for the first and second data types.

11. The method of claim 1, further comprising:
detecting at least one change in the data associated with the first and second data types; and
producing, on the haptic display, an updated vibration pattern to reflect the at least one change as detected.

12. A system for controlling a haptic display, comprising:
a processing unit; and
a non-transitory computer-readable medium having stored thereon computer-readable instructions executable by the processing unit for:
obtaining data associated with first and second data types, the data defining values for the first and second data types, the first data type relating to a first parameter of a plurality of measurable parameters associated with an operating environment of the haptic display, and the second data type relating to a second parameter of the plurality of parameters, the second parameter different from the first parameter;
associating the first and second data types to first and second vibration features of the haptic display, respectively, the second vibration feature different from the first vibration feature; and
producing, on the haptic display, a vibration pattern comprising a plurality of vibration pulses representing the first and second vibration features within a common time interval, the first vibration feature relating to a first parameter of the vibration pattern and the second vibration feature relating to a second parameter of the vibration pattern, wherein the first vibration feature is expressed based on the values of the data for the first data type and the second vibration feature is expressed based on the values of the data for the second data type.

13. The system of claim 12, wherein the producing of the vibration pattern comprises producing a count of vibration pulses within the common time interval at a vibration tempo, wherein the first vibration feature is the vibration tempo, and wherein the second vibration feature is the count of vibration pulses.

14. The system of claim 13, wherein the obtaining of the data associated with the first and second data types comprises obtaining a heart rate of a subject and a blood pressure of the subject.

15. The system of claim 13, the computer-readable instructions are executable for:
obtaining additional data associated with at least one third data type, the additional data defining additional values for the at least one third data type; and
associating the at least one third data type to at least one third vibration feature of the haptic display, the at least one third vibration feature different from the first and second vibration features;
wherein the producing, on the haptic display, of the vibration pattern comprises producing the plurality of vibration pulses to represent the at least one third vibration feature within the common time interval, wherein the at least one third vibration feature is expressed based on the additional values for the at least one third data type.

16. The system of claim 15, wherein the producing of the vibration pattern comprises producing a count of vibration pulses within the common time interval at a vibration tempo, wherein the first vibration feature is the vibration tempo, wherein the second vibration feature is the count of vibration pulses, and wherein one of the at least one third vibration features is a frequency composition of the vibration pulses.

17. The system of claim 16, wherein the obtaining of the data associated with the first and second data types comprises obtaining a heart rate of a subject and a blood pressure of the subject, and wherein the obtaining of the additional data associated with the at least one third data type comprises obtaining a level of peripheral oxygen saturation of the subject.

18. The system of claim 16, wherein the producing of the plurality of vibration pulses to represent the at least one third vibration feature within the common time interval comprises producing the vibration pulses with one of dissonant frequency compositions and consonant frequency compositions to express the additional values for the at least one third data type.

19. The system of claim 15, wherein the producing of the vibration pattern comprises producing a count of vibration pulses within the common time interval at a vibration tempo, wherein the first vibration feature is the vibration tempo, wherein the second vibration feature is the count of vibration pulses, and wherein one of the at least one third vibration features is an intensity of the vibration pulses.

20. The system of claim 12, wherein the first vibration feature being expressed based on the values of the data for the first data type comprises selecting one of a plurality of first discrete states of the first vibration feature based on the values of the data of the first data type, and wherein the second vibration feature being expressed based on the values of the data for the second data type comprises selecting one of a plurality of second discrete states of the second vibration feature.

21. The system of claim 20, wherein the first and second pluralities of discrete states are associated with low, normal, and high values for the data of the first and second data types relative to predetermined ranges for the first and second data types.

22. The system of claim 12, wherein the computer-readable instructions are further executable by the processing unit for:
    detecting at least one change in the data associated with the first and second data types; and
    producing, on the haptic display, an updated vibration pattern to reflect the at least one change as detected.

* * * * *